United States Patent [19]

Hoffarth

[11] Patent Number: 5,705,476
[45] Date of Patent: Jan. 6, 1998

[54] LOW-FOAMING WETTING AGENT CONSISTING OF VARIOUS ALKOXYLATED ALCOHOL MIXTURES

[75] Inventor: Gunther Hoffarth, Leverkusen, Germany

[73] Assignee: Bayer Aktiengesellschaft, Leverkusen, Germany

[21] Appl. No.: 772,192

[22] Filed: Dec. 20, 1996

Related U.S. Application Data

[63] Continuation of Ser. No. 432,540, May 2, 1995, abandoned.

[30] Foreign Application Priority Data

May 9, 1994 [DE] Germany .................. 44 16 303.7

[51] Int. Cl.$^6$ .................. C11D 1/825; C11D 1/72; C11D 1/722
[52] U.S. Cl. .................. 510/535; 510/360; 510/413; 510/422; 510/506
[58] Field of Search .................. 510/506, 360, 510/413, 421, 422, 514, 535

[56] References Cited

U.S. PATENT DOCUMENTS

| Re. 32,778 | 11/1988 | Hansen et al. | 252/61 |
|---|---|---|---|
| 3,882,038 | 5/1975 | Clayton et al. | 252/164 |
| 4,123,378 | 10/1978 | Abel et al. | 252/171 |
| 4,176,080 | 11/1979 | Wise et al. | 510/340 |
| 4,247,424 | 1/1981 | Kuzel et al. | 510/341 |
| 4,405,490 | 9/1983 | Maas et al. | 252/358 |
| 4,428,751 | 1/1984 | Via | 252/8.9 |
| 4,477,514 | 10/1984 | Gee et al. | 252/8.61 |
| 4,582,596 | 4/1986 | Hansen et al. | 252/61 |
| 4,648,984 | 3/1987 | Krause et al. | 252/174.22 |
| 4,692,260 | 9/1987 | Sung et al. | 252/99 |
| 4,780,237 | 10/1988 | Schmid et al. | 510/274 |
| 4,788,001 | 11/1988 | Narula | 106/287.13 |
| 5,061,393 | 10/1991 | Linares et al. | 510/424 |

FOREIGN PATENT DOCUMENTS

| 150 626 | 9/1981 | German Dem. Rep. |
|---|---|---|
| 251 689 | 11/1987 | German Dem. Rep. |
| 50 626 | 9/1981 | Germany . |
| 30 18 173 | 11/1981 | Germany . |
| 42 12 592 | 10/1993 | Germany . |
| 47-15923 | 5/1972 | Japan . |
| 59-122599 | 7/1984 | Japan . |
| 60-1296 | 1/1985 | Japan . |
| 60-38496 | 2/1985 | Japan . |
| 3-193997 | 8/1991 | Japan . |
| 891901 | 3/1962 | United Kingdom . |
| 1 489 484 | 10/1977 | United Kingdom . |

OTHER PUBLICATIONS

Chemical Abstracts, vol. 120, Abstract No. 325687u, pp. 119–120 (1994).

Primary Examiner—Ardith Hertzog
Attorney, Agent, or Firm—Sprung Kramer Schaefer & Briscoe

[57] ABSTRACT

Novel low-foaming wetting agents consisting of

I) 30 to 90% by weight of one or more substances of the formula $$R^1O\text{-}(EO)_m\text{-}H, \quad (Ia)$$

$$R^1O\text{-}(EO)_n\text{-}(PO)_o\text{-}H, \quad (Ib)$$

and/or $$R^1O\text{-}(PO)_p\text{-}(EO)_q\text{-}H, \quad (Ic)$$

and/or

II) 70 to 10% by weight of one or more substances of the formula $$R^2O\text{-}(PO)_r\text{-}H, \quad (II)$$

and

III) 0 to 30% by weight of one or more substances of the formula $$R^3O\text{-}(EO)_s\text{-}H \quad (III)$$

where all percentages given are based on the total weight of the wetting agent and where $R^1$ and $R^2$, independently of one another, denote straight-chain or branched $C_4$–$C_{20}$-alkyl, $C_4$–$C_{20}$-alkenyl, $C_5$–$C_8$-cycloalkyl, $C_6$–$C_{12}$-aryl which may be mono- to trisubstituted by $C_1$–$C_{12}$-alkyl, or denotes $C_7$–$C_{10}$-aralkyl, the aromatic portion of which may be mono- to trisubstituted by $C_1$–$C_4$-alkyl, $R^3$ denotes straight-chain or branched $C_{12}$–$C_{22}$-alkyl, $C_{12}$–$C_{22}$-alkenyl or phenyl which is substituted by 1 to 3 alkyl groups having a total of 6 to 12 C atoms, EO and PO denote ethylene oxide and propylene oxide units, respectively, m and r, independently of one another, are 1 to 30, preferably 1 to 20, n, o, p and q, independently of one another, are 1 to 10 and s is 15 to 50.

These wetting agents are used in aqueous liquors for textile processes, for the formulation of crop protection agents, and the like.

1 Claim, No Drawings

LOW-FOAMING WETTING AGENT CONSISTING OF VARIOUS ALKOXYLATED ALCOHOL MIXTURES

This application is a continuation of application Ser. No. 08/432,540, filed on May 2, 1995, now abandoned.

BACKGROUND OF THE INVENTION

The invention relates to low-foaming wetting agents consisting, on the one hand, of a mixture of alcohol or phenol ethoxylates or mixed ethoxylates/propoxylates and, on the other hand, of pure alcohol or phenol propoxylates. The invention furthermore relates to the use of such wetting agents in aqueous liquors used in textile processes, for formulating crop protection agents, and the like.

For a long time, anionic, cationic and non-ionic surfactants have been used individually or in combination with one another as wetting agents. Suitable non-ionic surfactants are mainly alkoxylates of longer-chain alcohols or phenols for example from the chemistry of fats, which are prepared by reacting such alcohols or phenols with ethylene oxide (EO) or ethylene oxide/propylene oxide (EO/PO). It is known that ethoxylates are highly foaming non-ionic wetting agents. It is also known that pure propoxylates, which are basically known, are essentially water-insoluble beyond a certain chain length of the hydrophobic alkyl moiety. This limit is reached at about 5 to 6 C atoms in the alkyl moiety. Accordingly, such propoxylates cannot be used in aqueous systems as wetting agents.

In order to repress the extensive foaming, which is undesirable in many applications, there has been no shortage of attempts to repress this foaming effect by means of additives, such as silicone compounds, phosphorus compounds, and the like. Furthermore, attempts have been made to react, in particular, long-chain alcohols with ethylene oxide and propylene oxide in different order. This resulted in lower-foaming products, but the remaining application properties, such as wetting effect, resistance to alkali foaming behaviour were adversely affected by this method.

SUMMARY OF THE INVENTION

Novel low-foaming wetting agents have now been found which consist of

I) 30 to 90% by weight of one or more substances of the formula

  (Ia)

  (Ib)

and/or

  (Ic)

II) 70 to 10% by weight of one or more substances of the formula

  (II)

and

III) 0 to 30% by weight of one or more substances of the formula

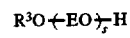  (III)

where all percentages given are based on the total weight of the wetting agent and where $R^1$ and $R^2$, independently of one another, denote straight-chain or branched $C_4$–$C_{20}$-alkyl, $C_4$–$C_{20}$-alkenyl, $C_5$–$C_8$-cycloalkyl, $C_6$–$C_{12}$-aryl which may be mono- to trisubstituted by $C_1$–$C_{12}$-alkyl, or denotes $C_7$–$C_{10}$-aralkyl, the aromatic portion of which may be mono- to trisubstituted by $C_1$–$C_4$-alkyl, $R^3$ denotes straight-chain or branched $C_{12}$–$C_{22}$-alkyl, $C_{12}$–$C_{22}$-alkenyl or phenyl which is substituted by 1 to 3 alkyl groups having a total of 6 to 12 C atoms, EO and PO denote ethylene oxide and propylene oxide units, respectively, m and r, independently of one another, are 1–30, preferably 1 to 20, n, o, p and q, independently of one another, are 1 to 10 and s is 15 to 50.

DETAILED DESCRIPTION OF THE INVENTION

It is surprising that the water-insoluble propoxylates of the formula (II) in combination with the alkoxylates of the formula (Ia) and/or (Ib) and/or (Ic) afford water-dispersible wetting agents distinguished by their low-foaming characteristics. Using pure propoxylates, which on the basis of the abovementioned insufficient water solubility did not seem possible for the purposes mentioned, results in advantages and simplifications when preparing the wetting agents according to the invention. Radicals $R^1$, $R^2$ and $R^3$ having 4 to 20 C atoms or 12 to 22 C atoms are known to one skilled in the art. The longer-chain radicals are known, for example, from the chemistry of fats; this applies in particular to those having an even number of C atoms and those which are straight-chain, that is unbranched. Apart from those (synthetic) alcohols in which the radicals $R^1$, $R^2$ and $R^3$ are straight-chain or branched and contain an even number or odd number of C atoms are of great importance.

Examples of $C_4$–$C_{20}$- or $C_{12}$–$C_{22}$-alkyl are butyl, i-butyl, pentyl, i-pentyl, neopentyl, hexyl, i-hexyl, octyl, i-octyl, 2-ethyl-hexyl, nonyl, i-nonyl, decyl, dodecyl, i-dodecyl, lauryl, palmityl, stearyl, eicosyl, heneicosyl, docosyl. An alkenyl having the same number of C atoms differs from the corresponding alkyl in that it contains a double bond.

Examples of $C_5$–$C_8$-cycloalkyl are cyclopentyl, cyclohexyl, methyl-cyclopentyl, cycloheptyl, methyl-cyclohexyl, dimethyl-cyclopentyl, cyclooctyl, dimethylcyclohexyl, trimethyl-cyclopentyl, ethyl-cyclohexyl. $C_6$–$C_{12}$-Aryl is phenyl, naphthyl or biphenylyl, preferably phenyl or naphthyl, particularly preferably phenyl; it can be mono- to trisubstituted by $C_1$–$C_{12}$-alkyl.

Examples of $C_7$–$C_{10}$-aralkyl are benzyl, α- or β-phenylethyl, phenyl-propyl or phenyl-butyl; in the aromatic moiety, it can also be mono- to trisubstituted by $C_1$–$C_4$-alkyl.

Preferred substances from groups I) and II) are those in which $R^1$ and $R^2$, independently of one another, denote $C_8$–$C_{16}$-alkyl, $C_6$–$C_{12}$-alkyl-phenyl or benzyl, the benzene ring of which can be mono- to trisubstituted by $C_1$–$C_4$-alkyl.

Particularly preferred substances from groups I) and II) are those in which $R^1$ and $R^2$, independently of one another, denote $C_{10}$–$C_{14}$-alkyl or $C_{16}$–$C_{12}$-alkyl-phenyl.

Preferred substances from group III) are those in which $R^3$ denotes $C_{14}$–$C_{20}$-alkyl or $C_{14}$–$C_{20}$-alkenyl.

Compounds of the formulae (Ia) and)or (Ib) and/or (Ic), (II) and (III) can be prepared in a manner known to one skilled in the art by reacting ethylene oxide or propylene oxide with aliphatic alcohols, cycloalkanols, phenols or aralkanols. The underlying alcohols, cycloalkanols, phenols or aralkanols are those of natural or industrial origin, such as butanol, i-butanol, pentanol, i-pentanol, hexanol, i-hexanol, octanol, i-octanol, 2-ethyl-1-hexanol, trimethylhexanol, isomeric decanols, undecanols, dodecanols and further straight-chain and branched homologues up to eicosanol and docosanol, cyclohexanol, phenol, cresol, nonyl-phenol, octenol and other unsaturated alcohols, benzyl alcohol, tri-isopropyl-phenol.

Preferably, the low-foaming wetting agents according to the invention consist of 40 to 75% by weight of I), 60 to 25% by weight of II) and 0 to 25% by weight of III), particularly preferably of 40 to 70% by weight of I), 30 to 60% by weight of II) and 0 to 20% by weight of III).

Furthermore, preference is given to those wetting agents according to the invention in which component I) consists of only one or more substances of the formula (Ia).

In a still further preferred embodiment, the relationship between the number of C atoms of component I) and the index m is such that the hydrophilic/lipophilic balance HLB ranges from 8 to 16, preferably from 9 to 15. The HLB is calculated by the following formula:

$$HLB = \frac{\text{mass of } EO \text{ units}}{\text{total mass of ethoxylate}} \cdot 20$$

For example, for a decyl alcohol which has been reacted with, on average, 6 EO units, the following value is obtained:

$$HLB = \frac{6 \times 44.05}{158.58 + 644.05} \cdot 20 = 12.51$$

44.05 = molecular weight of $EO$
158.28 = molecular weight of $C_{10}H_{21}OH$

In a manner known to those skilled in the art, the indices m to s are average values and can therefore also be intermediate values between integers. Thus, in the above arithmetic example an ethoxylate having on average 6 EO units can also contain small amounts of ethoxylates having a smaller number (for example 5 or only 4) or a larger number (for example 7 or 8) of EO units.

According to the above description, the low-foaming wetting agents according to the invention necessarily always consist of substances of the formula (Ia, b, c) and of the formula (II). However, it has been found that an additional content of substances of the formula (III) is favourable for some applications. Such an addition increases the resistance to alkali of the low-foaming wetting agents according to the invention containing components I) and II), the low-foaming characteristics not being diminished to an undesirable extent by adding III) within the range given. Such a resistance to alkali can be desirable, for example, when the low-foaming wetting agents according to the invention are used in alkaline bleaching processes. In other cases, the addition of component III) may be omitted. A suitable composition for rendering the low-foaming wetting agents according to the invention alkali-resistant is one consisting of 33 to 67% by weight of I), 67 to 33% by weight of II) and 5 to 20% by weight of III).

The wetting agents according to the invention are prepared by combining components I), II) and III) in any desired order and homogenizing them by stirring, kneading or measures having the same effect. They are then diluted with water to give the use form described below. For shipping and storage, the wetting agents can be used as such or in the form of an aqueous concentrate. Since the wetting agents are used anyway in an aqueous medium, it is possible, for ease of homogenization, also to add water in addition to I), II) and III) already during their preparation, resulting in a use form or a concentrate.

The low-foaming wetting agents according to the invention are used in aqueous liquors during textile processes, for formulating crop protection agents, and the like. The use in textile processes is of particular importance. Examples of such textile processes are dyeing and pre-treatment and after-treatment in conjunction with dyeing, furthermore bleaching processes and processes for textile finish, furthermore in water-repellent finish, oil-repellent finish and anti-static finish of textiles. Preferably, the low-foaming wetting agents according to the invention are used in processes of textile dyeing and pre-treatment for textile dyeing. Use concentrations are 0.02 to 0.5% by weight of wetting agent (total amount of I)+II)+III)) in the aqueous liquor; shipping and storage forms (concentrates) contain, for example, 20 to 100% by weight of I)+II)+III) (balance water).

EXAMPLES

The wetting agents listed below in group I (polyglycol alkyl ethers, alkylpolyethylene oxide/polypropylene oxide adducts or alkylpolypropylene oxide/polyethylene oxide adducts) and the antifoaming synergistic alkylpolypropylene oxides described in group II were prepared by methods customary in industry at 140° to 150° C./1 to 2 bar with KOH catalysis. The starting materials used were commercially available alcohols for example branched or unbranched $C_8$–$C_{16}$-alcohols.

Group I: Wetting agents of good wetting action which, however, are usually high-foaming and can therefore not be used under turbulent liquor ratios: (EO=mol of ethylene oxide, PO=tool of propylene oxide)

A) iso-decanol+4 EO
B) iso-decancil+6 EO
C) iso-decanol+8 EO
D) n-decanol+5 EO
E) n-decanol+5 EO+4 PO
F) n-decanol+7 EO+4 PO
G) iso-undecanol+5 EO
H) iso-dodecanol+6 EO
I) iso-tridecanol+6 EO
J) 2-ethylhexanol+8 PO+6 EO
K) oleyl alcohol+20 EO Group II: Alkylpolypropylene oxides (synergistic antifoams)

a) 2-ethylhexanol+2 PO
b) 2-ethylhexanol+6 PO
c) 2-ethylhexanol+10 PO
d) iso-octanol+6 PO
e) iso-nonanol+6 PO
f) iso-decanol+6 PO
g) iso-undecanol+6 PO
h) iso-dodecanol+6 PO
i) cyclohexanol+8 PO
j) benzyl alcohol+8 PO k) (for comparison: antifoam based on kerosene or rape oil)

The compounds of group I were tested for their wetting action, foaming behaviour and liquor stability, in particular in alkaline medium, first without additives and then in combination with the substances of group II. The results are shown in Tables 1) to 4) and clearly demonstrate the advantages of the combined wetting agents according to the invention.

The wetting action was tested by DIN 53901 (dip-wetting method), i.e. the time between immersion and sinking of a standardized small cotton test scarf in the test solution in seconds is measured (amounts used: 1 g of active substance/1 of $H_2O$). Rapid wetting agents range from 0 to 10 seconds and good wetting agents from 10 to 20 seconds.

The foaming behaviour was tested by the hole-disc method (method of Schlachter and Dierkes) which consists in moving a perforated metal disc attached to the end of a metal plunger at a uniform rhythm up and down in the test solution present in a glass cylinder and then rating the resulting foam. (The volume of foam in ml is measured after 50 strokes at time 0 and after ½, 1, 2 and 3 minutes. Amounts used: 1 g of active substance/1 of test solution; in the alkaline range with the addition of 1 g of sodium carbonate/1 of test solution).

The amount of foam acceptable in practice under liquor turbulences (for example in JET apparatuses) should not exceed 50 to 100 ml, while in other apparatuses up to 500 ml are still acceptable. Of still greater importance is the collapse of the resulting foam within the shortest possible period of time.

Abbreviations used in Tables 1) to 4) are:

$N_1$ wetting times in seconds in the neutral range (distilled $H_2O$)

$N_2$ wetting times in seconds in the alkaline range (15 ml/1 of 32% strength by weight NaOH)

$N_3$ wetting times in seconds upon addition of 40 g of sodium hydroxide/1 of test solution $S_1$ volume of foam in ml after 50 strokes in the neutral range $S_2$ volume of foam in ml after 50 strokes in the alkaline range (addition of 1 g of $Na_2CO_3/1$).

TABLE 1

Wetting action and foaming behaviour of the surfactants solely from group I (known non-ionic, high-foaming wetting agents)

| Substance | $N_1$ | $N_2$ | $S_1$ | $S_2$ |
|---|---|---|---|---|
| A) | 14 | 18 | *750, 650 | 600, 550 |
| B) | 13 | 17 | 950, 850 | 950, 900 |
| C) | 18 | 23 | 950, 900 | 1000, 950 |
| D) | 12 | 17 | 1000, 950 | 1100, 1000 |
| E) | 13 | 19 | 800, 500 | 750, 600 |
| F) | 21 | 24 | 900, 800 | 950, 850 |
| G) | 12 | 17 | 700, 650 | 750, 700 |
| H) | 13 | 14 | 800, 750 | 700, 650 |
| I) | 12 | 15 | 700, 650 | 800, 750 |
| J) | 18 | 22 | 650, 600 | 400, 350 |
| K) | >120 | >120 | 1000, 950 | 900, 850 |

*First value: initial amount of foam
Second value: volume of foam after ½ minute

TABLE 2

Wetting agent combinations according to the invention in a mixing ratio of 50/50 (percent by weight) from group I and group II

| Substance | $N_1$ | $N_2$ | $S_1$ | $S_2$ |
|---|---|---|---|---|
| A/b | 16 | 19 | *ed, 0 | *ed, 0 |
| B/b | 13 | 15 | 100, 0 | ed, 0 |
| C/b | 16 | 17 | 250, 0 | 300, 0 |
| D/b | 12 | 16 | 250, 150 | 200, 100 |
| E/b | 18 | 21 | 100, 0 | 300, 150 |
| F/b | 15 | 17 | 150, ed | 200, ed |
| G/b | 14 | 18 | 200, 100 | 150, 100 |
| H/b | 12 | 17 | 250, 150 | 200, 150 |
| I/b | 15 | 18 | 200, 150 | 150, 100 |
| J/b | 19 | 21 | 50, 0 | 100, 0 |
| K/b | 29 | 34 | 150, 50 | 200, 150 |

(*edge foam)

Table 2 clearly shows that the wetting agent combinations according to the invention are absolutely equivalent to the compounds of Table 1 in their wetting power but are significantly superior to them in their foaming behaviour.

Mixtures A/b, B/b and J/b can be used in JET apparatuses, and the combination K/b exhibits the most significant improvement compared with K by itself not only in the wetting action but also in the foaming behaviour.

TABLE 3

Wetting action and foaming behaviour of the wetting agents according to the invention as a function of the mixing ratio (90/10 to 20/80) of compounds A/b from product groups I and II.

| Substance (A/b ratio) | $N_1$ | $N_2$ | $S_1$ | $S_2$ |
|---|---|---|---|---|
| A(100%) | 14 | 18 | 750, 700 | 650, 550 |
| 90/10 | 12 | 14 | 250, 100 | 150, 50 |
| 80/20 | 15 | 17 | 150, 50 | 100, 50 |
| 70/30 | 11 | 13 | 150, ed | 100, ed |
| 60/40 | 13 | 16 | 50, 0 | 50, ed |
| 50/50 | 15 | 18 | ed, 0 | 50, 0 |
| 40/60 | 16 | 19 | ed, 0 | ed, 0 |
| 30/70 | 18 | 21 | ed, 0 | ed, 0 |
| 20/80 | 27 | 29 | oil droplets | oil film |

Table 3 clearly shows that the desired effect, that is foam reduction of the wetting agent solution without impairment of the wetting action, is observed at an A/b mixing ratio of as low as 90/10.

Increasing the proportion of the alkylpolypropylene oxide component b gives solutions having excellent foaming behaviour (suitable as wetting agent for JET apparatuses) while maintaining their good wetting times. Unstable liquors and, as a result thereof, a worsening of the wetting action is only observed at an A/b ratio such as 20/80.

TABLE 4

Wetting action and foaming behaviour of the wetting agent combination according to the invention as a function of the hydrocarbon chain and the number of PO units of the substances of group II (Example: substance B in a mixture with substances from group II; mixing ratio 50/50)

| Substance | $N_1$ | $N_2$ | $S_1$ | $S_2$ |
|---|---|---|---|---|
| B (100%) | 13 | 17 | 950, 850 | 950, 900 |
| B/a | 10 | 12 | ed, 0 | 100, ed |
| B/b | 13 | 15 | 100, 0 | ed, 0 |
| B/c | 15 | 16 | 200, 0 | 200, ed |

TABLE 4-continued

Wetting action and foaming behaviour of the wetting agent combination according to the invention as a function of the hydrocarbon chain and the number of PO units of the substances of group II (Example: substance B in a mixture with substances from group II; mixing ratio 50/50)

| Substance | $N_1$ | $N_2$ | $S_1$ | $S_2$ |
|---|---|---|---|---|
| B/d | 19 | 22 | 250, ed | 200, 0 |
| B/e | 16 | 19 | 100, 0 | 150, ed |
| B/f | 18 | 21 | 100, 0 | 50, 0 |
| B/g | 21 | 23 | 100, 0 | 50, 0 |
| B/h | 22 | 25 | 150, 0 | 100, 0 |
| B/i | 24 | 26 | 200, ed | 150, ed |
| B/j | 27 | 29 | 150, ed | 100, ed |
| *B/k | 46 | 57[1] | 250, ed | 200, 0 |
|  | 53 | 68[2] | 300, 200 | 400, 350 |

[1] commercially available antifoam based on kerosene.
[2] commercially available antifoam based on rape oil.

Table 4 shows that very good results are obtained with PO derivatives of alcohols of chain length $C_8$ to $C_{10}$, it also being possible for the PO units to be varied over a wide range (see B/a, B/b, B/c). When commercially available antifoams (for example based on hydrocarbons or fatty acid esters) are mixed, a foam reduction is only achieved in combination with a substantial worsening of the wetting action.

TABLE 5

Improvement of the wetting action in a strongly alkaline medium by addition of substances from product group III to the wetting agent combinations listed in Table 2 (Example 2 from Table 2)

| Substance | $N_1$ | $N_2$ | $N_3$ |
|---|---|---|---|
| B/b (Comparison) | 13 | 15 | 52 |
| 90% B/b 10% K | 17 | 19 | 36 |
| 80% B/b 20% K | 20 | 23 | 21 |

More than 30% of K does not give an additional improvement of the wetting action but leads to a substantial worsening of the foaming behaviour.

What is claimed is:
1. Low-foaming wetting agent consisting of
   I) 30 to 67% by weight of one or more compounds of the formula

$$R^1O{\mathrm{-}}(EO)_m{\mathrm{-}}H, \qquad (Ia)$$

$$R^1O{\mathrm{-}}(EO)_n{\mathrm{-}}(PO)_o{\mathrm{-}}H, \qquad (Ib)$$

or $$R^1O{\mathrm{-}}(PO)_p{\mathrm{-}}(EO)_q{\mathrm{-}}H, \qquad (Ic)$$

component I) exhibiting a hydrophilic/lipophilic balance HLB ranging from 8 to 16,
   II) 67 to 33% by weight of one or more compounds of the formula $$R^2O{\mathrm{-}}(PO)_r{\mathrm{-}}H, \qquad (II)$$

III) 0 to 30% by weight of one or more compounds of the formula $$R^3O{\mathrm{-}}(EO)_s{\mathrm{-}}H \qquad (III)$$

where all percentages given are based on the total weight of the wetting agent and where
   $R^1$ and $R^2$ are each independently selected from the group consisting of straight-chain or branched $C_4$–$C_{20}$-alkyl, or straight-chain or branched $C_4$–$C_{20}$-alkenyl, or $C_5$–$C_8$cycloalkyl,
   $R^3$ denotes straight-chain or branched $C_{12}$–$C_{22}$-alkyl, or $C_{12}$–$C_{22}$-alkenyl,
   EO and PO denote ethylene oxide and propylene oxide units, respectively,
   m denotes 1 to 30,
   r denotes 2 to 30,
   n, o, p and q, independently of one another, are 1 to 10 and
   s is 15 to 50.

* * * * *